(12) United States Patent
Dumm (10) Patent No.: US 9,357,798 B2
(45) Date of Patent: Jun. 7, 2016

(54) PROOF OF TREATMENT CLOSURE AND METHODS OF USE

(71) Applicant: Richard H Dumm, Windsor, CO (US)

(72) Inventor: Richard H Dumm, Windsor, CO (US)

( * ) Notice: Subject to any disclaimer, the term of this patent is extended or adjusted under 35 U.S.C. 154(b) by 0 days.

(21) Appl. No.: 14/429,430

(22) PCT Filed: Nov. 28, 2012

(86) PCT No.: PCT/US2012/066814
§ 371 (c)(1),
(2) Date: Mar. 19, 2015

(87) PCT Pub. No.: WO2014/007838
PCT Pub. Date: Jan. 9, 2014

(65) Prior Publication Data
US 2015/0223511 A1    Aug. 13, 2015

Related U.S. Application Data (60) Provisional application No. 61/667,308, filed on Jul. 2, 2012.

(51) Int. Cl.
*A23C 3/023* (2006.01)
*A23L 3/00* (2006.01)
*C12Q 1/26* (2006.01)
*C12Q 1/58* (2006.01)
*C12Q 1/66* (2006.01)

(52) U.S. Cl.
CPC ............... *A23L 3/003* (2013.01); *A23C 3/023* (2013.01); *C12Q 1/26* (2013.01); *C12Q 1/58* (2013.01); *C12Q 1/66* (2013.01); *A23V 2002/00* (2013.01)

(58) Field of Classification Search
CPC .... A23C 3/023; A23L 3/003; A23V 2002/00; C12Q 1/26; C12Q 1/58; C12Q 1/66
USPC ............ 206/459.1; 215/230, 203; 422/82.12; 220/592.01, 288; 374/141, 163, 155, 374/149, 150, 208, 120, 130, 131, 121, 148, 374/144; 383/207, 208, 209, 66; 426/126, 426/132, 231, 87, 88; 116/216
See application file for complete search history.

(56) References Cited

U.S. PATENT DOCUMENTS

| | | | | |
|---|---|---|---|---|
| 3,468,978 A | * | 9/1969 | Battersby | C09J 123/04 156/334 |
| 4,284,672 A | * | 8/1981 | Stillman | B32B 15/08 206/524.2 |
| 5,799,606 A | | 9/1998 | Volk | |
| 5,911,665 A | * | 6/1999 | Heydarpour | B32B 27/08 426/126 |

(Continued)

*Primary Examiner* — Erik Kashnikow
*Assistant Examiner* — Ericson M Lachica
(74) *Attorney, Agent, or Firm* — Leyendecker & Lemire LLC (57) ABSTRACT

Proof of treatment closures for vessels and methods of use of the closures are described. Embodiments the closures indicate that vessel contents have reached at least a predetermined temperature. The proof of treatment closures can show that vessel contents a distance within the vessel interior have reached the threshold conditions, rather than reflecting conditions of the vessel itself, or of vessel contents in close proximity to a vessel peripheral boundary. Embodiments include proof of treatment closures resistant to status tampering, such that it is difficult to activate the indicator without reaching the specified conditions. The proof of treatment closures can also be seal tamper evident, such that loosening or removing the closure from the vessel, or otherwise breaking a seal between the closure and the vessel, leaves conspicuous evidence of such.

14 Claims, 12 Drawing Sheets

(56) References Cited

U.S. PATENT DOCUMENTS

| | | | |
|---|---|---|---|
| 2003/0042220 A1* | 3/2003 | Bourreau | B65D 41/0492 215/349 |
| 2003/0155361 A1* | 8/2003 | Jones | B65D 41/0414 220/288 |
| 2006/0078717 A1* | 4/2006 | Yamaya | C08G 77/50 428/212 |
| 2008/0135563 A1* | 6/2008 | Hickey | G01K 13/00 220/592.01 |
| 2009/0092519 A1* | 4/2009 | Stewart | F03G 7/06 422/82.12 |
| 2012/0325769 A1* | 12/2012 | Essebaggers | B65D 47/248 215/256 |

* cited by examiner

PROOF OF TREATMENT CLOSURE AND METHODS OF USE

This application claims priority to and incorporates by reference, U.S. patent application No. 61/667,308, filed 2 Jul. 2012, having the same inventor and title as the present application.

In addition, the present application incorporates by reference in their entirety but does not claim priority to, the following US patent applications and issued patents, with which the present application shares a common inventor: U.S. patent application Ser. No. 12/584,522, filed 8 Sep. 2009; U.S. Pat. No. 6,276,264 filed 24 Oct. 2000 and issued 6 Aug. 2001; and U.S. Pat. No. 7,401,546, filed 20 Aug. 2004 and issued 2 Jul. 2008.

BACKGROUND

Dairy products generally require pasteurization in order to ensure safe consumption. Other foods and beverages can also benefit from specific heat treatments that contribute to consumer safety. Even under refrigerated storage, unpasteurized dairy products can relatively rapidly become unpalatable, unsafe, or otherwise unfit for consumption due to proliferation of viable bacteria in the refrigerated products. Moreover, dairy products can sometimes contain microbes that are pathogenic in humans and other animals. Treating the dairy products containing pathogenic microbes at pasteurizing temperatures can reduce or eliminate the microbes, and thereby reduce pathogenicity, providing for safer consumption of the treated products.

Visual confirmation that dairy products have been pasteurized would be advantageous, particularly in regions where dairy products that are contaminated by pathogenic microbes or are inadequately pasteurized are prevalent. In some regions, lack of a robust regulatory regime can contribute to such prevalence, and even where oversight is typically adequate, the consumers and vendors may prefer having visual confirmation that a particular process has occurred. Accordingly, a visual indicator that shows whether dairy products in a vessel have been sufficiently heat pasteurized in that vessel is desirable. Where the temperature indicator is resistant to tampering or indicates that tampering has occurred, it becomes a more reliable gauge of dairy product safety.

DETAILED DESCRIPTION

Embodiments of the present invention include proof of treatment closures for vessels, wherein the closures indicate that vessel contents have reached at least a predetermined temperature. The proof of treatment closure shows that the predetermined temperature has been reached at some point rather than indicating real time temperature of vessel contents. In some embodiments, the predetermined temperature must be reached for at least a specified time in order to activate the proof of treatment closure.

The proof of treatment closure can show that vessel contents a distance within the vessel interior have reached the threshold conditions, rather than reflecting conditions of the vessel itself, or of vessel contents in close proximity to a vessel peripheral boundary such as a vessel wall or spout. The vessel contents are typically, but not necessarily, dairy products. In some embodiments, the proof of treatment closure is deployed at or above a predetermined temperature of 160° F. to 162° F., which is generally considered sufficient to pasteurize milk. Variations require that at least the predetermined temperature be maintained for a minimum time interval in order for the proof of treatment closure to be deployed. For instance, a minimum time interval of 15-30 seconds can be optimal for pasteurizing milk. The term "undeployed" refers to devices that have not been deployed, rather than devices that have been deployed and then reset. Deployment is typically, but not necessarily, irreversible.

Embodiments include proof of treatment closures resistant to status tampering, such that it is difficult to activate the indicator without reaching the specified conditions. The proof of treatment closures can also be seal tamper evident, such that loosening or removing the closure from the vessel, or otherwise breaking a seal between the closure and the vessel, leaves evidence of such. In some embodiments, the proof of treatment closure must be in an undeployed state in order to be installed on a vessel.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given, except when referring to temperature, where "approximately" means plus or minus 2.0° F.

The term "about," as used in this specification and appended claims, refers to plus or minus 20% of the value given, except when referring to temperature, where "about" means plus or minus 4.0° F.

The terms "generally" and "substantially," as used in this specification and appended claims, mean mostly, or for the most part.

The terms "removable", "removably coupled", "removably disposed," "readily removable", "readily detachable", "detachably coupled", "separable," "separably coupled," and similar terms, as used in this specification and appended claims, refer to structures that can be uncoupled, detached, uninstalled, or removed from an adjoining structure with relative ease (i.e., non-destructively, and without a complicated or time-consuming process), and that can also be readily reinstalled, reattached, or coupled to the previously adjoining structure. A proof of treatment closure or cap can be both removable and seal tamper evident. Accordingly, the closure or cap may be structurally altered or nominally damaged where seal security is breached by disturbing or removing the closure or component from a vessel, but the closure or cap is still considered removable.

The term "soften," as used in this specification and appended claims, refers to a material changing from a solid physical state to a semi-solid or liquid state that occurs as the material melts or begins to melt.

The term "low visibility," as used in this specification and appended claims, refers to visibility of a flag, signal portion, or other indication device when a temperature indication closure is in a position or orientation that is relatively inconspicuous, especially in comparison to a high visibility position or orientation. The flag, signal portion, or other indication device is difficult or impossible to see when in a low visibility condition. For instance, where the flag of the first embodiment proof of treatment closure is in the first position, the closure is in an undeployed state and the flag is in a condition of "low visibility." The flag is therefore either impossible to see within the closure, or an observer peering into the window of the closure might be able to vaguely discern or detect the presence of the flag. Conversely, where the flag of the first embodiment proof of treatment closure is in the second position, the flag is "highly visible" or in a condition of "high visibility," such that the flag is conspicuously visible through the window of the closure. A condition of "low visibility" typically, but not necessarily, occurs where a proof of treatment closure is in an undeployed state.

The terms "highly visible," "high visibility," and similar terms, as used in this specification and appended claims, refer to a relatively conspicuous position or orientation of a flag, signal portion, or other indication device, especially in comparison to a low visibility position or orientation. For instance, where the flag of the first embodiment proof of treatment closure is in the second position, the closure is in a deployed state and the flag is in a condition of "high visibility." The flag is therefore much more visible than when the flag is in the low visibility first position. A condition of "high visibility" typically, but not necessarily, occurs where a proof of treatment closure is in a deployed state. However, in some embodiments, high visibility occurs where a proof of treatment closure is undeployed, and low visibility results from deployment.

A deployed first proof of treatment closure typically shows that vessel contents have reached at least a minimum temperature, and the vessel contents are thus pasteurized. In this circumstance, deployment indicates vessel contents are suitable for storage, consumption, or other intended purpose.

Conversely, in some embodiments a deployed proof of treatment closure can indicate, among other things, improper storage of heat labile products or inadequate refrigeration. Here, a deployed proof of treatment closure indicates that vessel contents are unsuitable for their intended purpose.

A First Embodiment Proof of Treatment Closure

Figure 1:
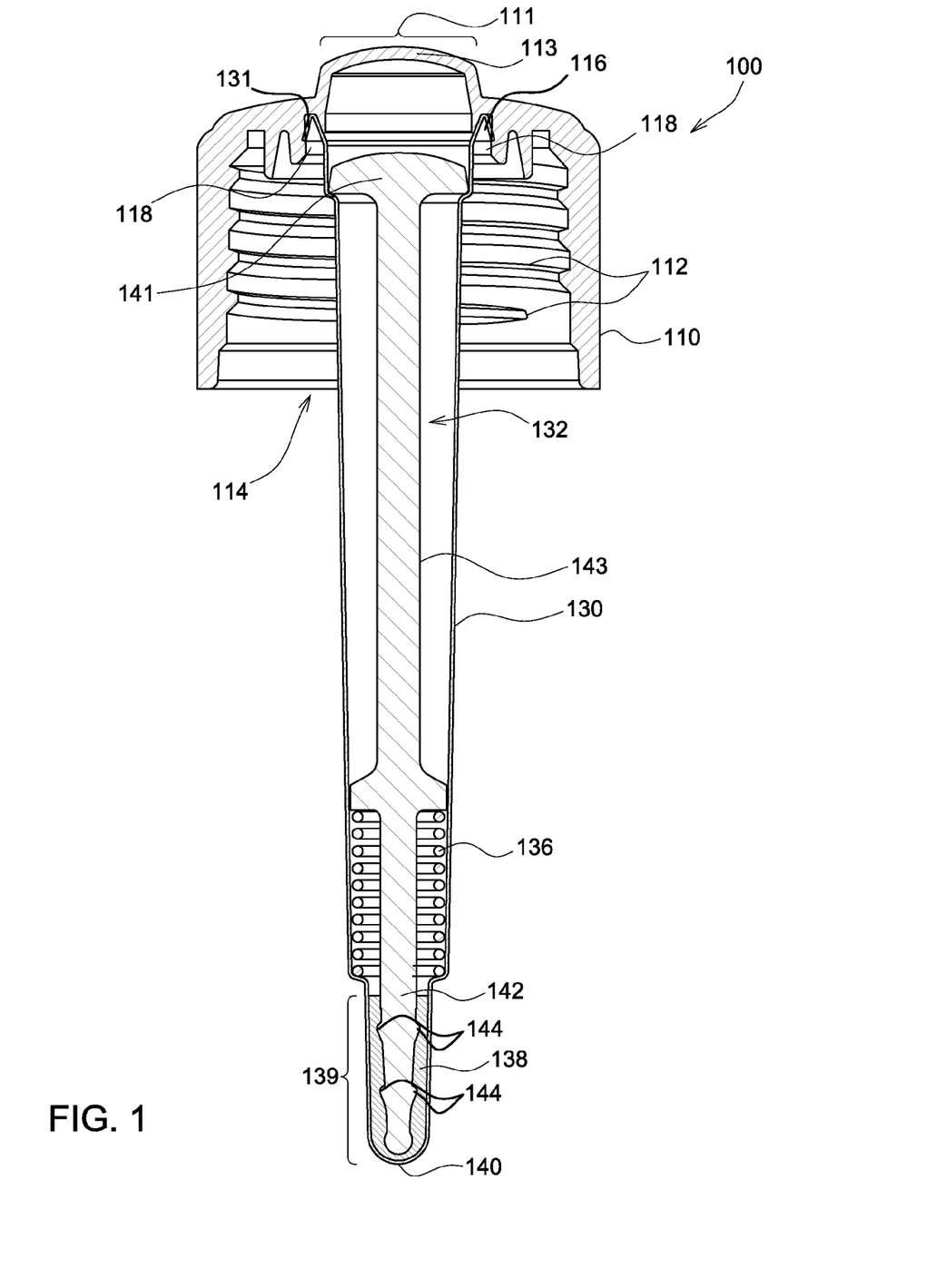
FIG. 1 is a side, cross-section view of a proof of treatment closure according to an embodiment of the present invention.
Figure 2:
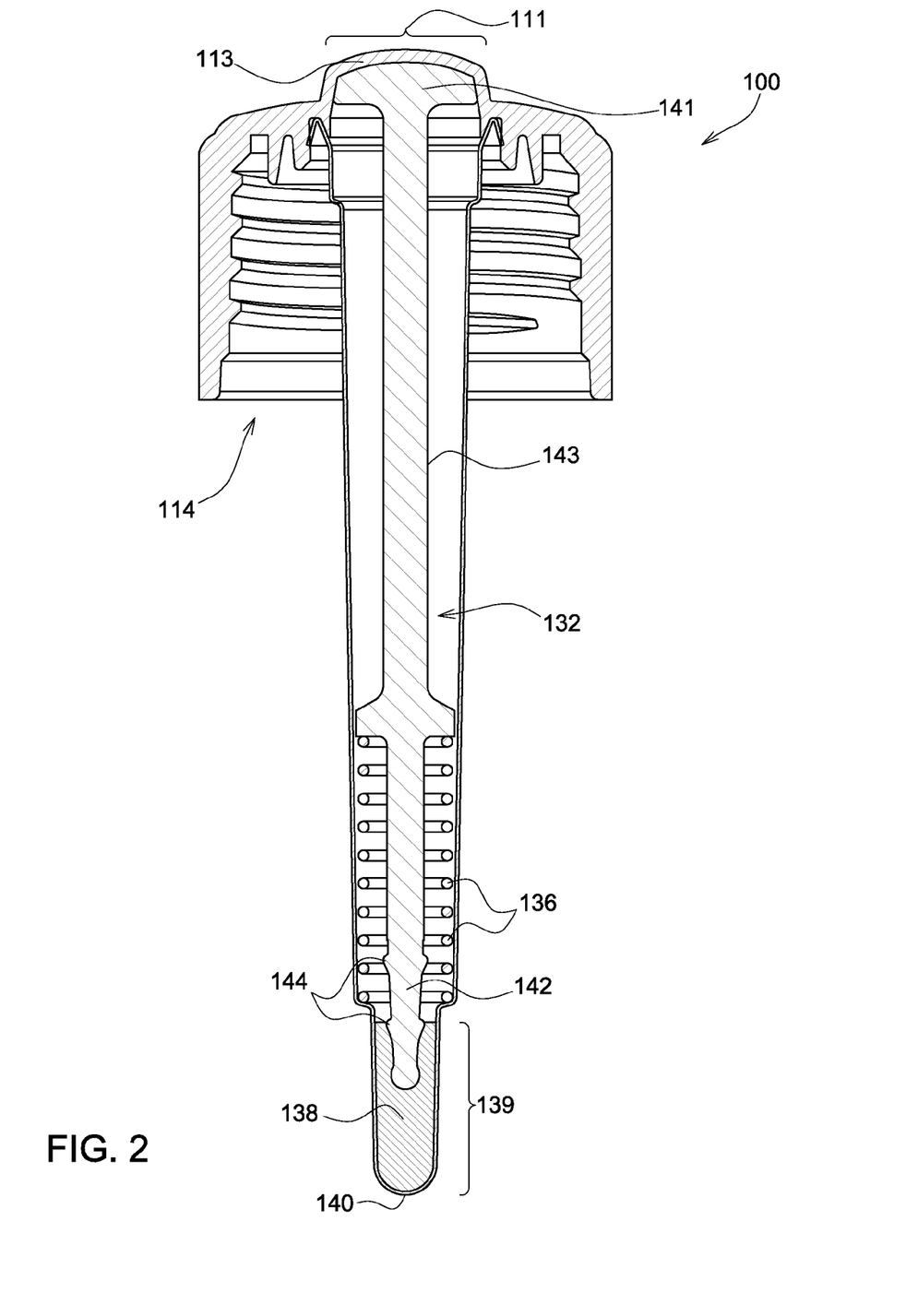
FIG. 2 is a side, cross-section view of a proof of treatment closure according to an embodiment of the present invention.

A first embodiment proof of treatment closure 100, illustrated in FIGS. 1 and 2, comprises a cap 110 directly coupled to a barrel 130. The cap 110 includes a window 111, internal (female) threads 112, and a spout receiving cavity 114 within which reside the internal threads 112. The first embodiment cap 110 comprises or consists essentially of one or more polymers. The term polymer or polymers includes copolymers.

The spout receiving cavity 114 is configured to receive a vessel spout and the internal threads 112 are configured to engage external (male) threads on the spout. The threaded coupling makes the cap 110 readily removable from the vessel spout. Other cap/vessel spout combinations can have other coupling mechanisms. For example, in some embodiments, the cap has external threads and the vessel spout has internal threads. Variations include, but are not limited to, friction fit and twist-lock couplings, cam lock devices, and bayonet connections.

The cap 110 further comprises a flange receiving cavity 116 and a tab 118 disposed proximate the flange receiving cavity. The flange receiving cavity 116 is configured to receive a barrel flange 131. The cap 110 and barrel 130 are illustrated assembled, wherein the barrel flange 131 resides in the flange receiving cavity 116, thereby coupling the barrel 130 to the cap 110. During assembly, in order to gain access to the flange receiving cavity 116, the barrel flange 131 pushes aside the tab 118. The cap 110 is generally sufficiently pliant to deform slightly and permit the tab 118 to be pushed aside by the barrel flange during assembly, and sufficiently resilient for the tab to return to its original position. Accordingly, after the barrel flange 131 has entered the flange receiving cavity 116, the tab 118 returns to its original position, whereupon the barrel flange 131 is secured with in the flange receiving cavity 116. Further, hoop stresses imparted to the flange receiving tab 118 by the barrel flange 131, typically induce a condition known as "creep" of the flange receiving tab 118 around relatively noncompliant material of the metal barrel flange 131. An undercut condition usually results, further ensuring secure retention of the barrel 130 into the cap 100.

The barrel 130 of the first embodiment consists essentially of aluminum alloy. Embodiments include other metals or metal alloy barrels, including but not limited to stainless steel. Metal barrels are typically, but not necessarily, manufactured through a deep draw process. In some embodiments, the barrel consists essentially of or comprises a polymer. Embodiments of metal barrels can be coated with polymers including, but not limited to, polyolefins or polyethylene terephthalate (PET), which are generally well suited to contact vessel contents without adversely affecting product safety, stability, or palatability.

The proof of treatment closure 100 further comprises a flag 132, a spring 136, and a transition medium 138. The transition medium 138 resides within a temperature sensing region 139 of the proof of treatment closure 100. The temperature sensing region 139 is typically, but not necessarily, disposed adjacent to the barrel distal terminus 140.

The flag 132 includes a signal portion 141 and an anchor portion 142 connected by a shaft 143. The anchor portion 142 includes capture features 144 configured to be gripped by the transition medium 138. The capture features 144 of the first embodiment can be characterized as barbs. Other capture features include, but are not limited to rings, ridges, dimples, surface texture, bumps, through-holes, loops, and sintering. The spring 136 of the first embodiment is a compression spring and the transition medium is a wax. Embodiments comprise transition media including, but not limited to, food grade wax, relatively low melting point salts, and relatively low melting point metals and metal alloys. The transition medium of the first embodiment softens when heated to a predetermined temperature of at least 160° F. to 162° F. for not less than 30 seconds.

The proof of treatment closure 100 is shown in the undeployed state in FIG. 1, and in the deployed state in FIG. 2. As shown in FIG. 1, in the undeployed state the flag 132 resides in a first position wherein the anchor portion 142 of the flag 132 resides surrounded by the transition medium 138 within the temperature sensing region 139. When below a predetermined temperature, the transition medium 138 is a solid or semi-solid that grips the anchor portion 142, thereby securing the anchor portion within the transition medium and thus maintaining the flag 132 in the first position and the proof of treatment closure in an undeployed state.

In the undeployed state, as shown in FIG. 1, the signal portion 141 has poor visibility because it is separated from the window 111 by an air gap, and the window includes a translucent lens 113 that scatters light and obscures or partially obscures the signal portion 141. The translucent lens 113 of the first embodiment comprises a polymer. In some embodiments, the window includes a transparent lens. Variations include a window lacking a lens. Embodiments include a window comprising an uncovered aperture providing a view into or through the cap.

The transition medium 138 is adapted to soften or melt at a predetermined temperature, whereupon purchase of the transition medium on the anchor portion 142 becomes insufficient to overcome the force of the spring 136 to hold the flag 132 in the first position. Accordingly, the spring 136 forces the flag 132 upwardly in the barrel 130 to a second position, as shown in FIG. 2, wherein the signal portion 141 of the flag resides immediately proximate or in direct contact with the lens 113.

Thus the transition medium serves as a sensor for detecting a temperature threshold. Where the proof of treatment closure is installed on a vessel with the barrel extending into a vessel internal cavity, the transition medium is a sensor adapted to detect that vessel contents have reached at least a predetermined temperature. The vessel contents are typically fluids. The fluids are usually liquids, and the liquids are typically, but not necessarily, dairy products.

The signal portion 141 of the flag 132 of the first embodiment can be coated with a thin film of oil, which enhances visibility through the lens 113 when the signal portion is in contact therewith. Where only a thin film of oil resides between the signal portion and the lens, such that both the signal portion and the lens have direct contact with the thin film, the flag is considered to have direct contact with the lens for the purposes of this specification and appended claims.

As shown in FIG. 2, when the flag 132 resides in the second position, the signal portion 141 of the flag is highly visible, and the proof of treatment closure is thus in a deployed state. The signal portion 141 of the first embodiment is typically, but not necessarily, red, and the red color is conspicuously visible through the window 111 in the deployed state. Conversely, the color is scarcely discernable or not visible at all through the window 111 where the proof of treatment closure is in the undeployed state shown in FIG. 1. Embodiments include various colors of flags, including white, and different flag colors are sometimes used to indicate different treatment conditions that cause the proof of treatment closures to deploy.

The first embodiment proof of treatment closure 100 is resistant to status tampering because closure components, including the flag 143, spring 136, and transition medium 138, are inaccessibly sequestered within the closure. Accordingly, the flag is highly resistant to being physically altered in order to move the flag from the first position to the second position, and the closure is thus very difficult to change from an undeployed state to a deployed state, without subjecting the closure to at least the predetermined temperature or conspicuously damaging the closure.

A Second Embodiment Proof of Treatment Closure

Figure 3:
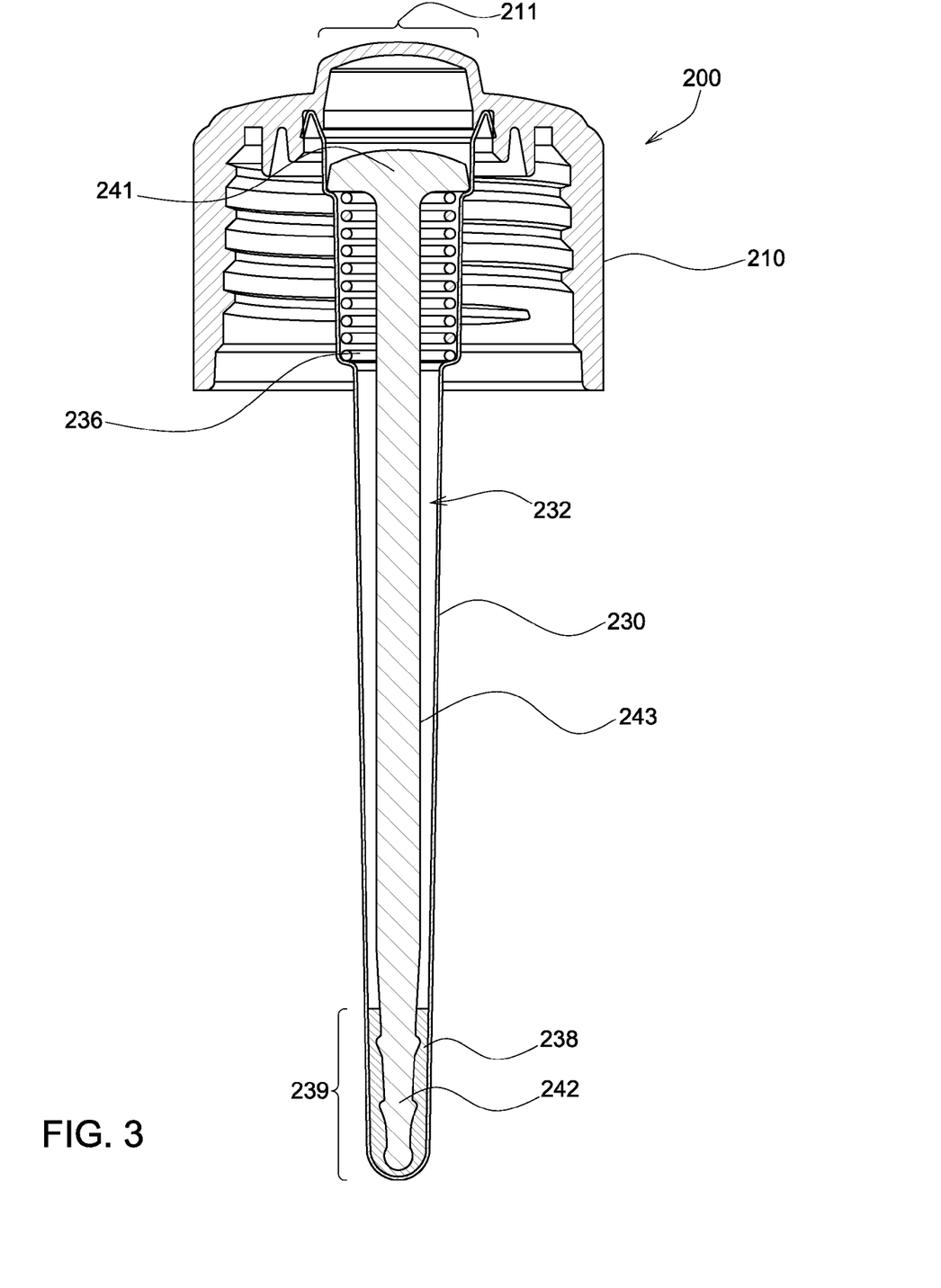
FIG. 3 is a side, cross-section view of a proof of treatment closure according to an embodiment of the present invention.

A second embodiment proof of treatment closure 200, illustrated in FIG. 3, is both functionally and structurally similar to the first embodiment 100. The second embodiment proof of treatment closure 200 comprises a cap 210 directly coupled to a metal barrel 230. The cap 210 includes a window 211, internal threads, and a spout receiving cavity providing access to the internal threads. The second embodiment further includes a flag 232 comprising a signal portion 241 and an anchor portion 242 joined by a shaft 243.

As with the first embodiment, the second embodiment anchor portion 242 is held fast within a transition medium 238, where the flag resides in a first position, as shown in FIG. 3. The transition medium resides within a sensing region 239 of the barrel 230.

A structural difference between the second embodiment 200 and the first embodiment 100 includes the spring 236 of the second embodiment residing relatively high on the barrel 230, whereas the first embodiment spring 136 resides proximate the barrel distal terminus 140. Functionally, the second embodiment proof of treatment closure 200 performs like the first embodiment 100. Accordingly, as a result of the transition medium 238 rising to at least a minimum temperature, the spring 236 forces the flag 232 from the first position to a second position as the transition medium 238 softens or melts and loses its purchase on the flag anchor portion 242.

A Third Embodiment Proof of Treatment Closure

Figure 4:
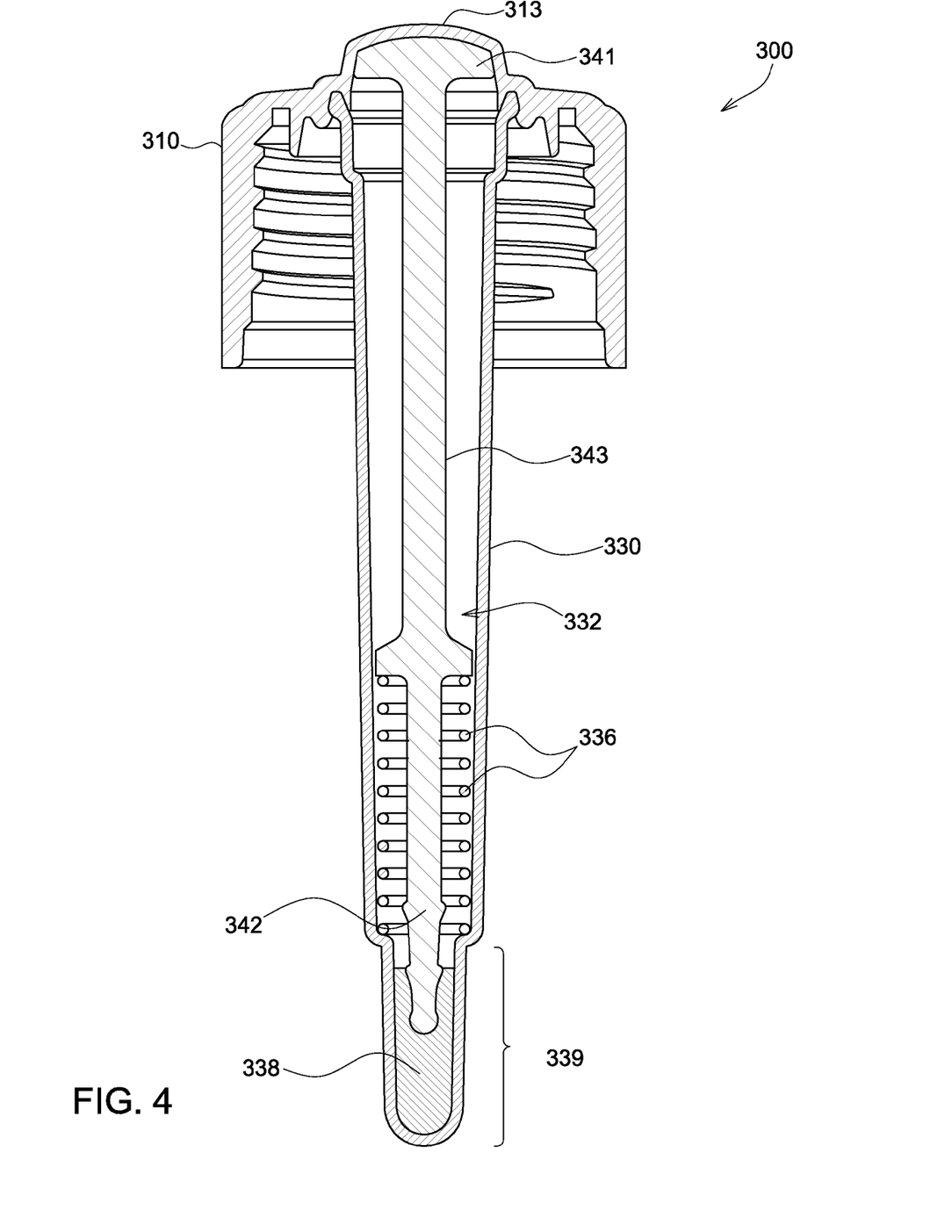
FIG. 4 is a side, cross-section view of a proof of treatment closure according to an embodiment of the present invention.

A third embodiment proof of treatment closure 300, illustrated in FIG. 4, is both functionally and structurally similar to the first embodiment 100. The third embodiment proof of treatment closure 300 comprises a cap 310 directly coupled to a barrel 330. The cap 310 includes a window comprising a translucent lens 313, internal threads, and a spout receiving cavity providing access to the internal threads. The third embodiment further includes a flag 332 comprising a signal portion 341 and an anchor portion 342 joined by a shaft 343.

As with the first embodiment 100, the anchor portion 342 of the third embodiment 300 is held fast within a transition medium 338 when the flag resides in its first position (not shown.). The transition medium resides within a sensing region 339 of the barrel 330.

A structural difference between the third embodiment 300 and the first embodiment 100 includes the barrel 330 of the third embodiment consisting essentially of a polymer, whereas the barrel 130 of the first embodiment 100 is mostly metal. Functionally, the third embodiment proof of treatment closure 300 performs like the first embodiment 100 and the second embodiment 200, with the spring 336 forcing the flag from the first position to a second position when the transition medium 338 softens or melts as a result of attaining a minimum temperature and the medium 338. FIG. 4 illustrates the third embodiment proof of treatment closure 300 in a deployed state, with the flag 332 residing in the second position.

Both the cap 310 and the barrel 330 of the third embodiment can be made of materials including acrylonitrile butadiene styrene (ABS), polystyrene, substituted polystyrenes, or polycarbonates. The third embodiment barrel 330 is solvent welded to the cap 310, and the solvent used for the welding is typically, but not necessarily, methyl ethyl ketone (MEK). In a method of making the third embodiment proof of treatment closure, solvent is delivered to a barrel receiving receptacle (not shown) of the cap, and the barrel 330 is subsequently inserted into the receptacle, with the barrel and cap consequently being welded together. The solvent can be delivered to the receptacle by use of a syringe or other pinpoint applicator. In some embodiments, the barrel can be dipped in solvent and then inserted into the receptacle while a barrel surface is soft, tacky, or wet with solvent. Solvent fusing methods can include capillary action to transport the solvent into a micro-gap between two surfaces. Variations include other welding methods for jointing barrels and caps, including but not limited to, ultrasonic welding, thermal welding, and welding through use of electromagnetic radiation. Radio frequency welding is an example of welding through use of electromagnetic radiation.

Materials used for a cap or barrel of a temperature a proof of treatment closure include metals, metal alloys, composites, high impact plastics, thermoplastics, natural polymers, and synthetic polymers. Polymers include, but are not limited to, nylon, polyvinyl chloride (PVC), ABS, PET, polystyrene, high impact polystyrene, polyetheretherketone (PEEK), polyimide, polycarbonate, polyaniline, acrylate or methacrylate polymers, fluorinated polymers such as polytetrafluoroethylene or polyfluoroethylenepropylene, and polyolefins such as polyethylene (PE), polypropylene (PP) and polybutylene (PB). Composites include, but are not limited to, carbon or glass fibers imbedded in resin. The resin can include polyesters, epoxies, and other suitable resins.

A Fourth Embodiment Proof of Treatment Closure

Figure 5:
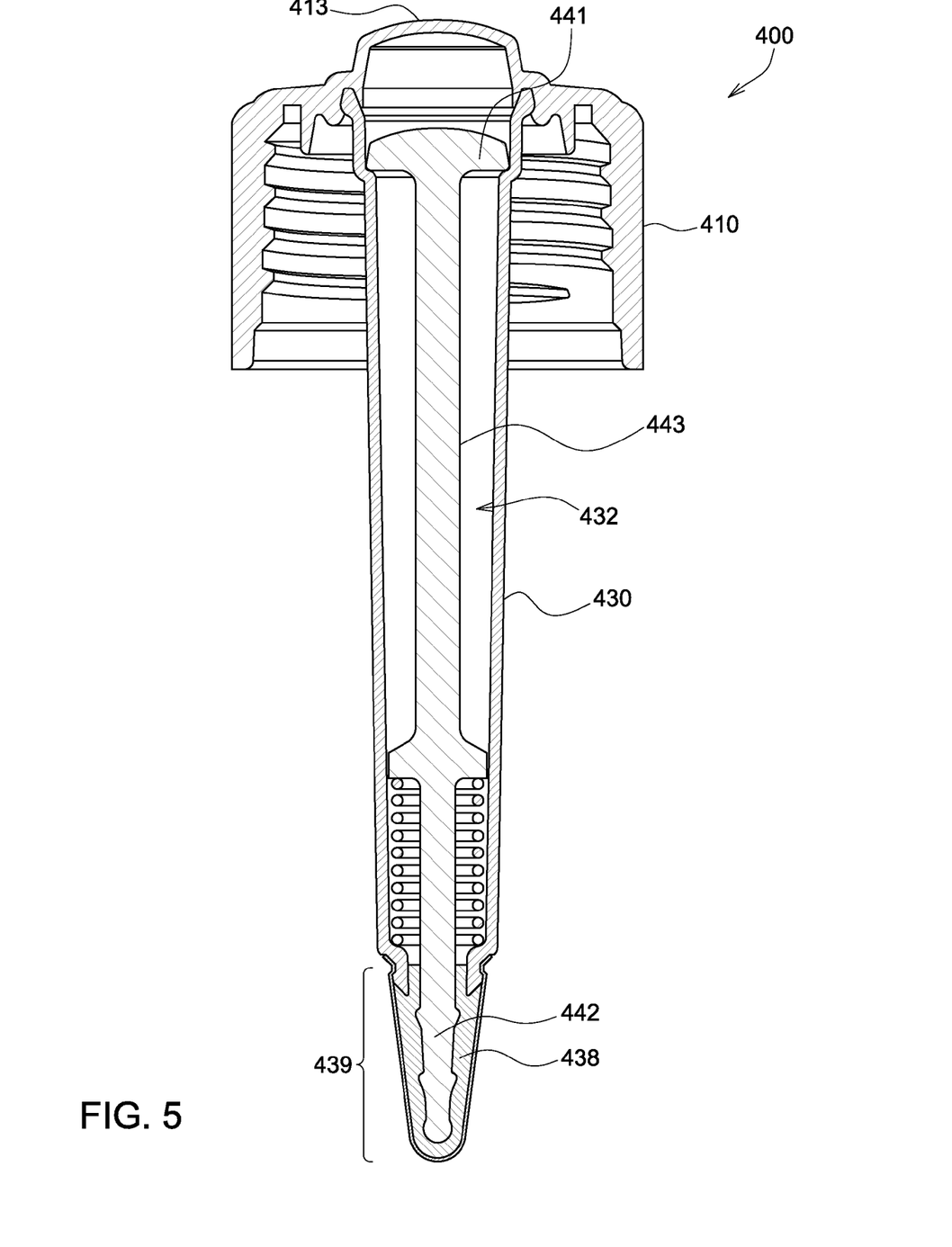
FIG. 5 is a side, cross-section view of a proof of treatment closure according to an embodiment of the present invention.

A fourth embodiment proof of treatment closure 400, illustrated in FIG. 5, is both functionally and structurally similar to the first embodiment 100. The fourth embodiment proof of treatment closure 400 comprises a cap 410 directly coupled to a barrel 430. The cap 410 includes a window comprising a translucent lens 413, internal threads, and a spout receiving cavity providing access to the internal threads. The third embodiment further includes a flag 432 comprising a signal portion 441 and an anchor portion 442 joined by a shaft 443.

The anchor portion 442 is held fast within a transition medium 438 when the flag 432 resides in a first position, as shown in FIG. 5. The transition medium resides within a sensing region 439 of the barrel 430. Unlike the first, second, and third embodiments, where the barrels are unitary structures including sensing regions integral with the barrel, the fourth embodiment sensing region 439 generally comprises aluminum alloy, and the aluminum alloy sensing region 439 is coupled to a polymeric barrel 430. The aluminum alloy of the sensing region generally conducts heat better than polymers, which can make the fourth embodiment sensing region respond more rapidly than polymeric embodiments.

A Fifth Embodiment Proof of Treatment Closure

Figure 6:
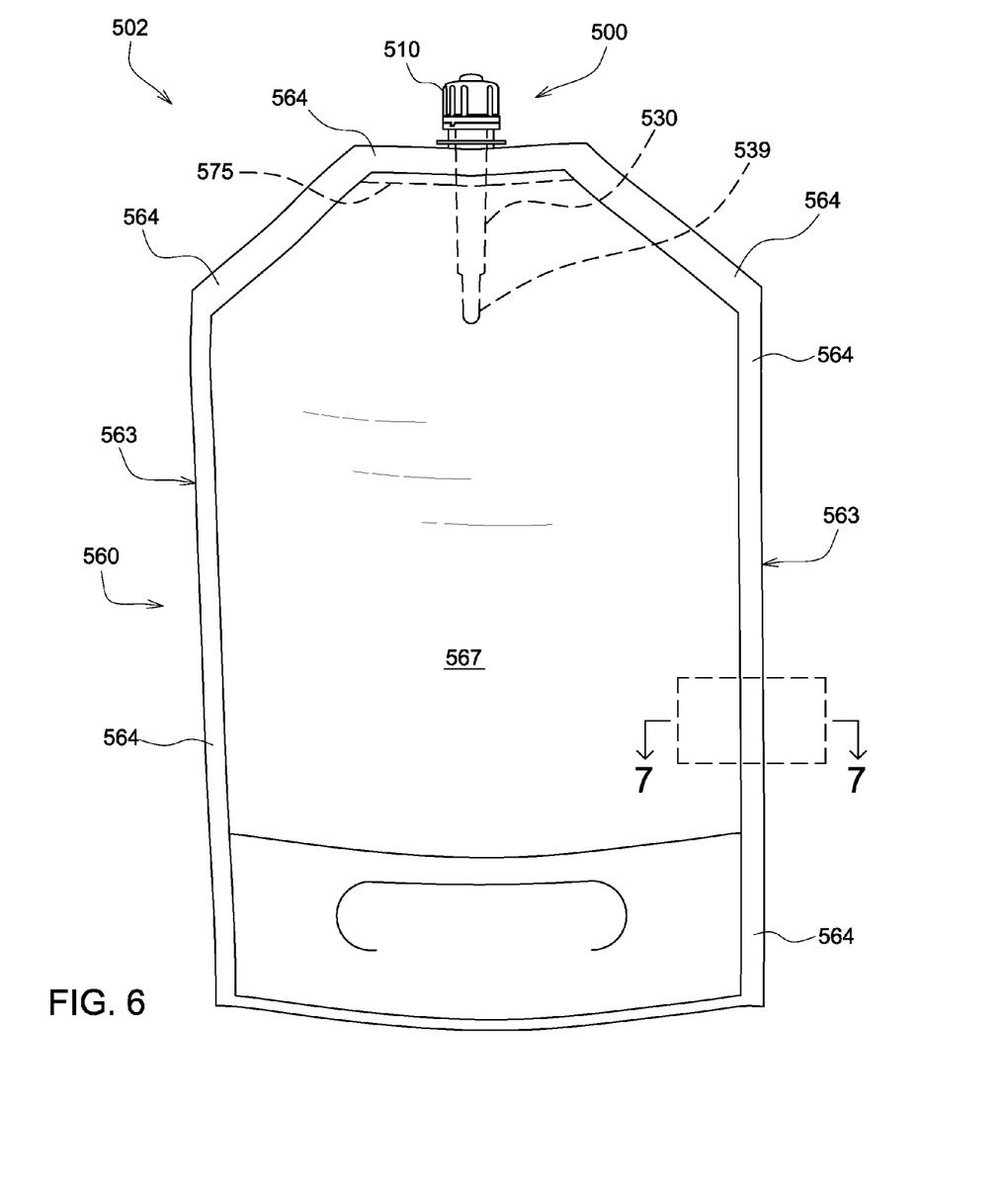
FIG. 6 is a side, orthogonal view of a proof of treatment closure installed on a vessel according to an embodiment of the present invention.
Figure 7:
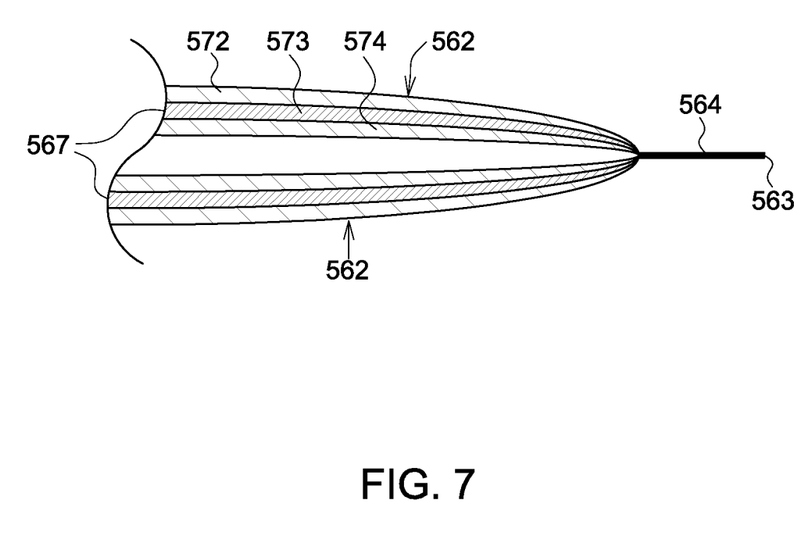
FIG. 7 is a partial sectional view of the vessel of FIG. 6 according to an embodiment of the present invention.
Figure 8:
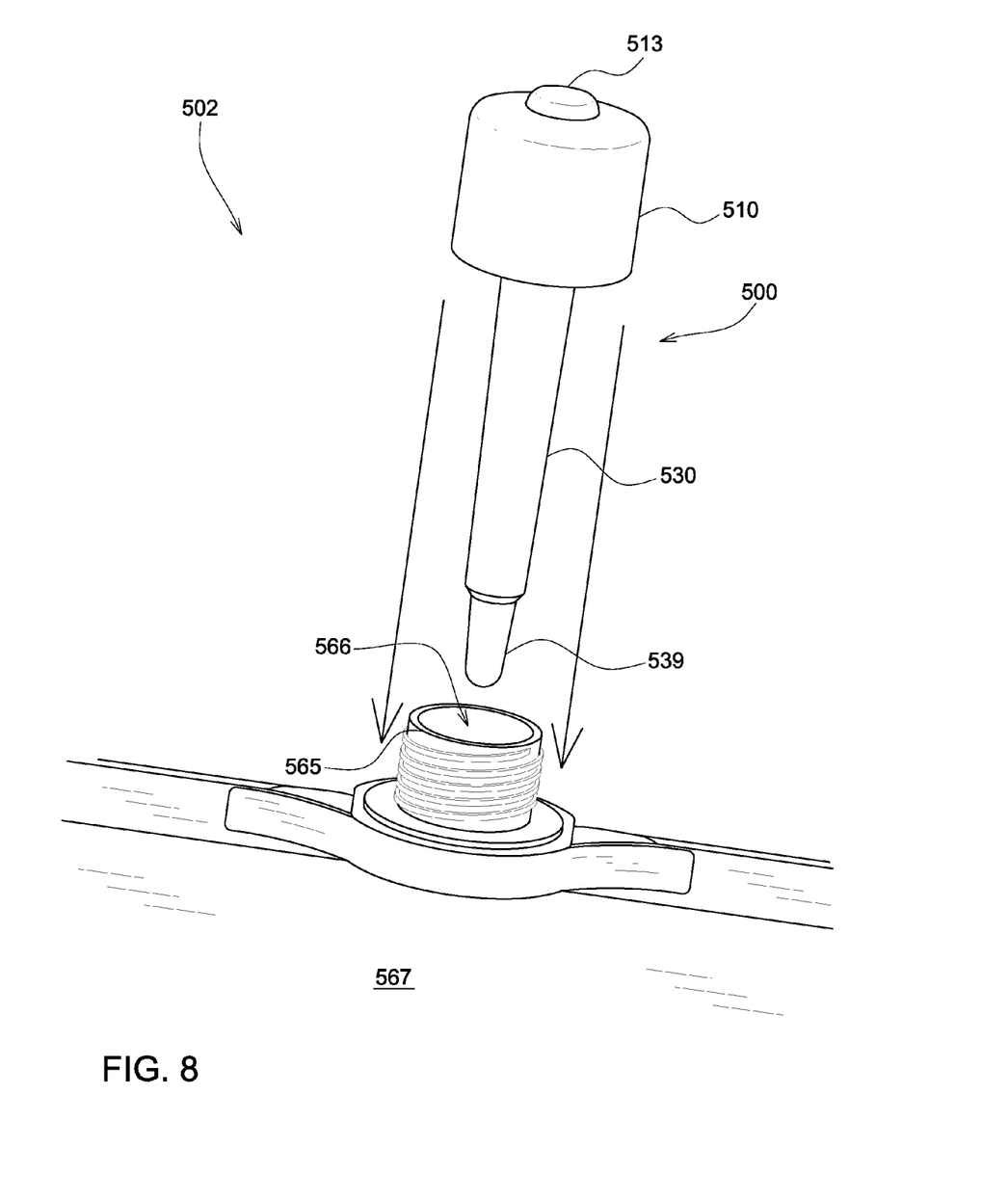
FIG. 8 is a perspective view of a proof of treatment closure and a vessel according to an embodiment of the present invention.
Figure 9:
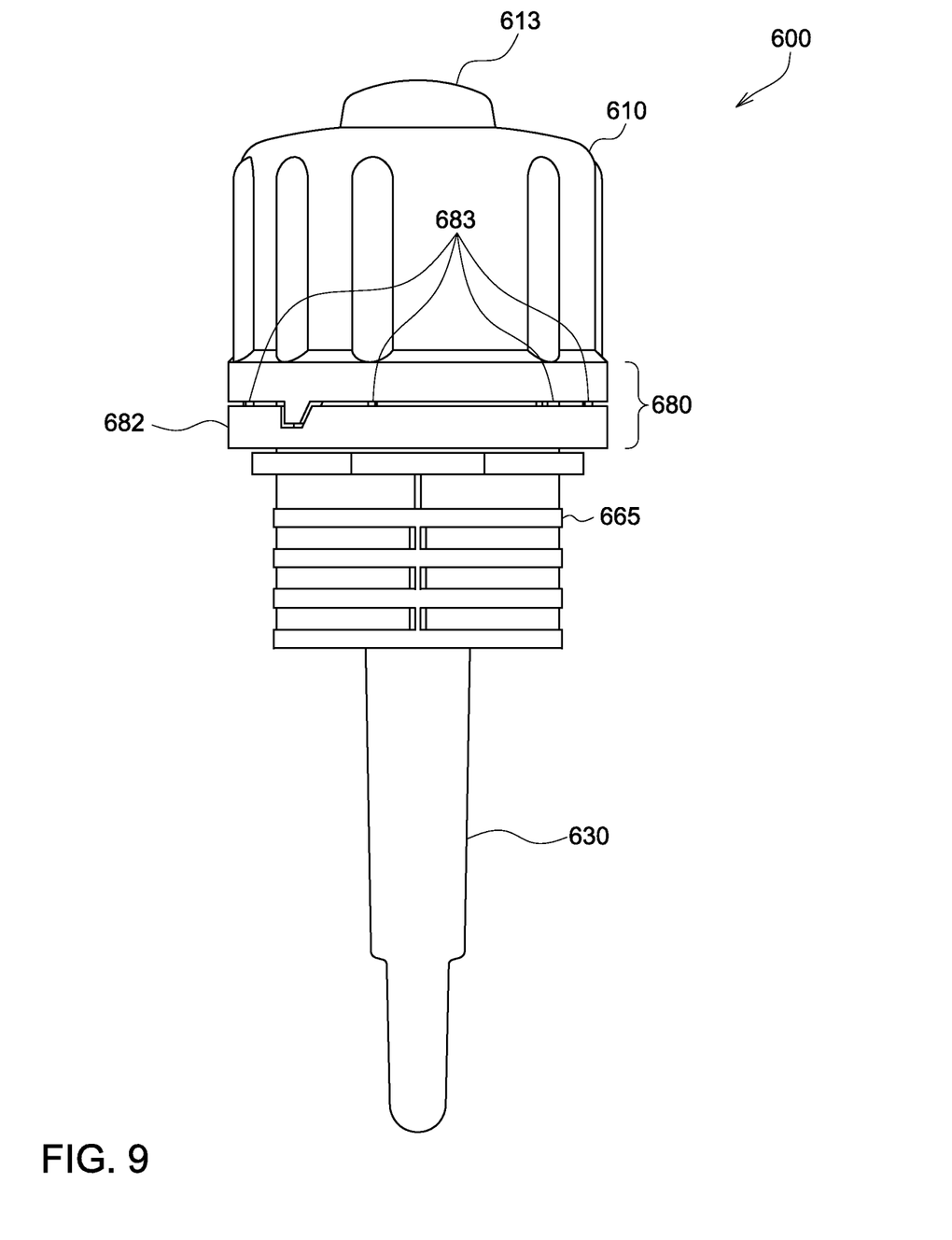
FIG. 9 is a side, orthogonal view of a proof of treatment closure according to an embodiment of the present invention.

A fifth embodiment proof of treatment closure 500 is illustrated in FIGS. 6-8 as part of a combination 502 that also includes a vessel 560. The closure 500 includes a cap 510 and a barrel 530, with a sensing region 539 of the barrel disposed proximate a barrel distal terminus. The cap 510 further comprises a translucent lens 513. The barrel 530 extends into a vessel interior cavity 566 by about 2.0 inches. Accordingly, the fifth embodiment proof of treatment closure 500 is configured to monitor liquid vessel contents 575 even where vessel is not full to the brim with the liquid contents.

Variations include proof of treatment closures whose components extend into vessel interior cavities preferably at least 0.50 inch, more preferably between 0.50 inch and 6.0 inches, still more preferably between 1.0 inch and 5.0 inches, and most preferably about 2.5 inches. Accordingly, embodiments of proof of treatment closures are configured to monitor liquid vessel contents that reside preferably at least 0.50 inch, more preferably between 0.50 inch and 6.0 inches, still more preferably between 1.0 inch and 5.0 inches, and most preferably about 2.5 inches inside the vessel interior cavity.

The vessel 560 comprises two vessel walls 562 that converge proximate a vessel periphery 563 where the converging vessel walls 562 are heat sealed together to form a flat seam 564. As best seen in a partial section view of the vessel illustrated in FIG. 7, the two vessel walls 562 comprise a flexible, heat-conductive laminate 567 including a heat conductive middle layer 573 sandwiched between two polymer layers. The heat-conductive middle layer typically comprises aluminum foil or other metal foil. An inner polymer layer 574 typically consists essentially of polyolefin (polyethylene) and an outer polymer layer 572 typically consists essentially of PET. The vessel further comprises a threaded spout 565.

Most heat conducting capability of the heat-conductive laminate resides in the metal foil middle layer 573. However, non heat-conductive laminates comprising metal foil layers are known in the art, the non heat-conductive laminates generally including a polymer layer configured to provide insulation by being relatively thick, including gas pockets, including a woven fabric, or by other insulation enhancing means.

A close-up exploded view of the combination 502 is illustrated in FIG. 8, which illustrates the externally threaded spout 565. The proof of treatment closure 500 screws on to the spout 565 and forms a hermetic seal therewith.

A Sixth Embodiment Proof of Treatment Closure

A sixth embodiment proof of treatment closure 600, illustrated in FIGS. 9-12, includes a cap 610, barrel 630, translucent lens 613, and a tamper evident assembly 680. The tamper evident assembly provides for a tamper evident seal with a vessel spout 665, such that a breakaway ring 682 must be torn from the cap 610 in order to break a hermetic seal between the cap 610 and the spout 665. The breakaway ring 682 is coupled to the cap with multiple breakable tabs 683.

Figure 10:
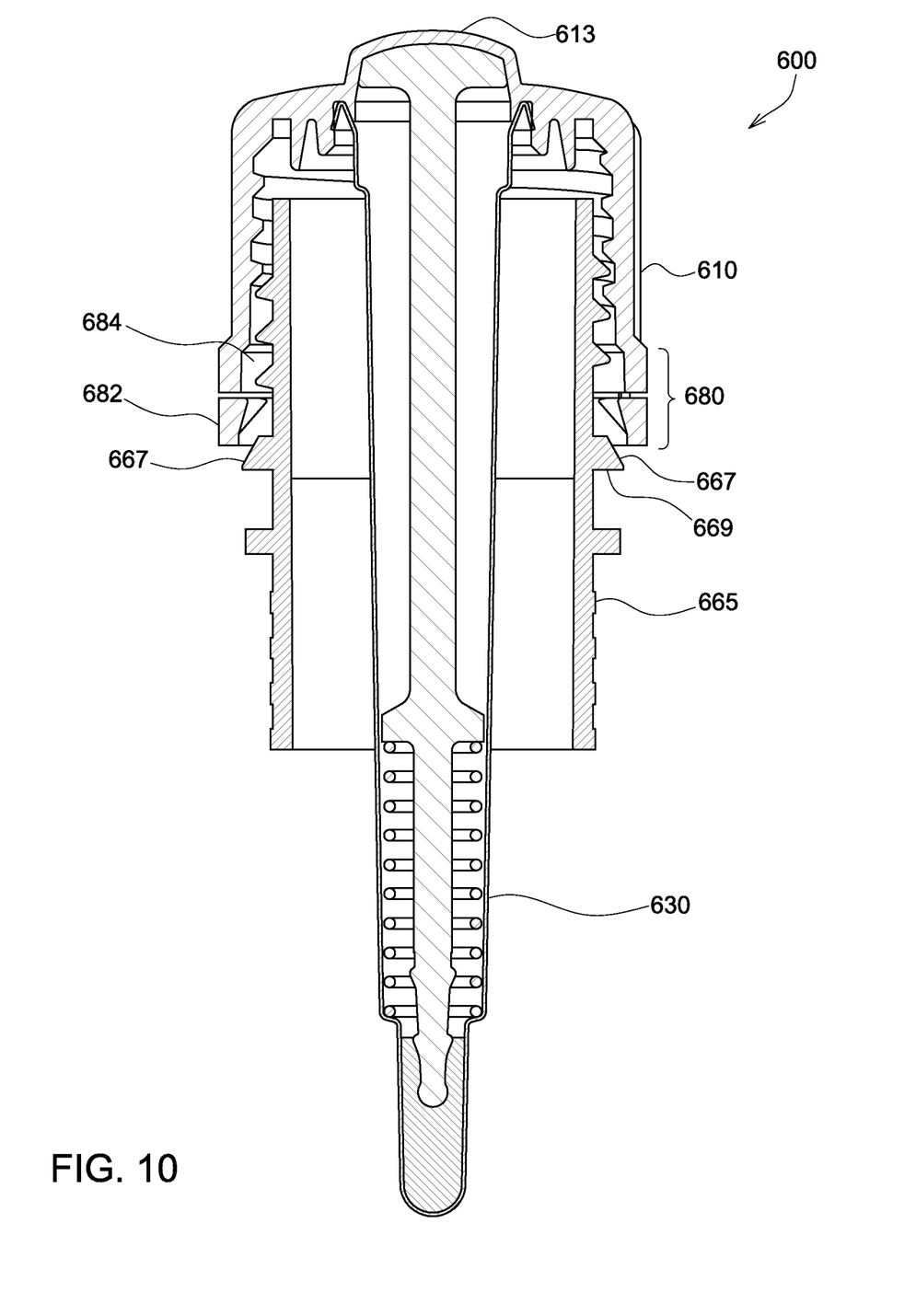
FIG. 10 is a side, cross-section view of a proof of treatment closure according to an embodiment of the present invention.
Figure 11:
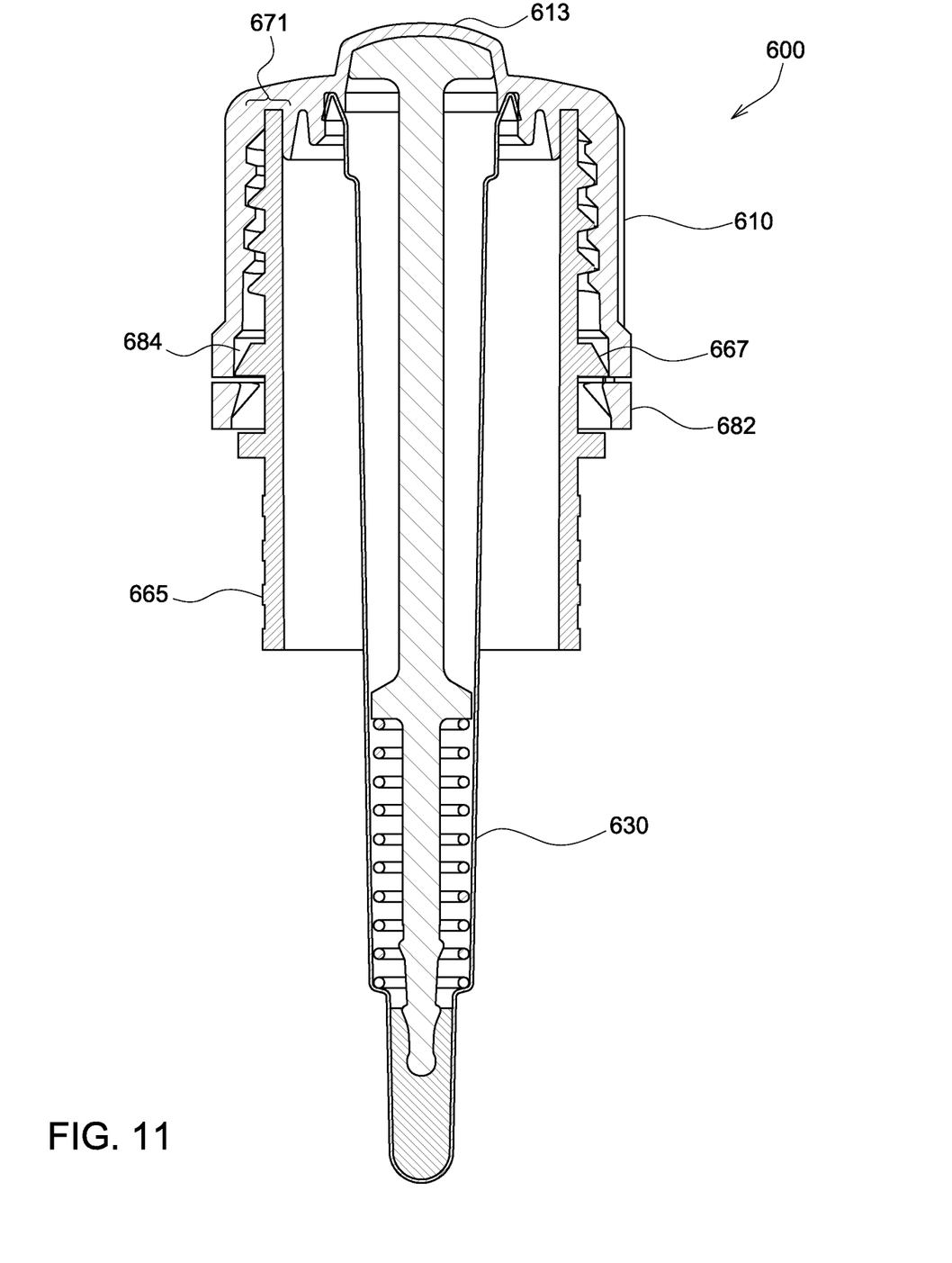
FIG. 11 is a side, cross-section view of a proof of treatment closure according to an embodiment of the present invention.

FIG. 10 shows the proof of treatment closure 600 partially installed on a spout 665. The tamper evident assembly 680 includes a protrusion receptacle 684 configured to receive an annular protrusion 667 disposed on the spout 665. FIG. 11 shows the closure 600 fully installed on the spout 665, with the annular protrusion 667 residing in the protrusion receptacle 684 and the breakaway ring 682 disposed below the protrusion 667. A beveled first surface of the annular protrusion 667 is configured to deflect the breakaway ring 682 as the cap 610 threads onto the spout 665 during installation of the closure 600 on a vessel, thereby allowing the ring 682 to slide over the protrusion 667 until the protrusion 667 enters the receptacle 684 and the breakaway ring 682 moves into place below the protrusion 667. Such installation results in a hermetic seal 671 forming between the vessel spout 665 and the cap 610.

Conversely, a flat lower surface 669 of the annular protrusion 667 prevents the breakaway ring 682 from sliding back over the protrusion 667 when the cap 610 is unscrewed to remove the proof of treatment closure 600 from a vessel. The breakaway ring 682 therefore breaks free of the cap 610 during removal, providing an irreversible visual indication that the hermetic seal between the cap 610 and the spout 665 has been broken.

Figure 12:
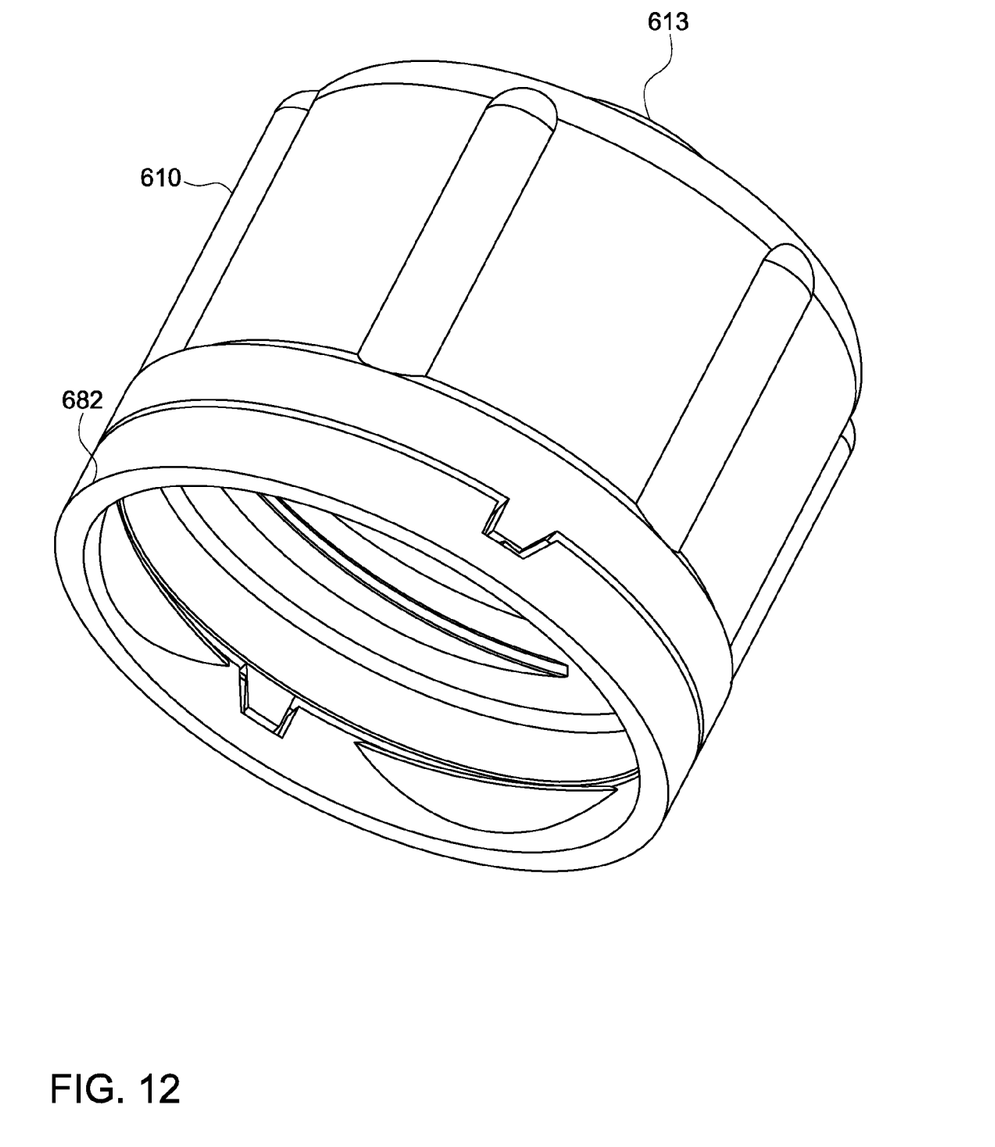
FIG. 12 is a perspective view of a proof of treatment closure according to an embodiment of the present invention.

FIG. 12 shows the cap 610 uninstalled on a vessel or spout, with the barrel omitted, in order to better illustrate the breakaway ring 682.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A combination comprising:
a vessel comprising an internal cavity, vessel walls, a spout, and vessel contents residing in the internal cavity;
a proof of treatment closure having an undeployed state and a deployed state, a distinction between the undeployed state and the deployed state being visible from outside the vessel, the proof of treatment closure including:
　a cap coupled directly to the spout and forming a hermetic seal therewith, wherein the cap includes a window having a transparent or translucent lens;
　a sensor residing within the internal cavity and at least 20 mm from the spout, wherein a change from the undeployed state to the deployed state is irreversibly achieved by heating the sensor to at least a predetermined temperature;
　a barrel coupled to the cap and extending at least 20 mm into the vessel; and
　a flag including a signal portion, the flag residing (i) in a first position when the proof of treatment closure is in the undeployed state, and (ii) in a second position when the proof of treatment closure is in the deployed state;
　wherein the signal portion (i) has low visibility when the flag is in the first position, and (ii) is highly visible through the window in the cap when the flag is in the second position;
　wherein (i) when the flag is in the first position, a lower portion of the flag is surrounded by a transition medium and the signal portion is located away from the window in the cap, and (ii) when the flag is in the second position, the signal portion is proximate to the window in the cap;
　wherein a thin film of liquid resides between the flag and the lens when the flag is in the second position.

2. The combination of claim 1, wherein the flag is resistant to status tampering.

3. The combination of claim 1, wherein:
the flag resides within the barrel when the flag is in the first position;
the sensor comprises the transition medium adapted to undergo a physical change at the predetermined temperature; and
the flag further comprises an anchor portion, the anchor portion (i) being secured in the transition medium when the flag is in the first position, and (ii) moving within the transition medium when the flag changes to the second position.

4. The combination of claim 2, wherein the coupling between the cap and the spout is seal tamper evident.

5. The combination of claim 4, wherein the spout is threaded and the cap is threadably coupled thereto.

6. The combination of claim 2, wherein the vessel is flexible and collapsible, and the vessel walls comprise a heat conductive laminate including an inner thermoplastic polymer layer, a middle metal foil layer, and an outer polymer layer.

7. The combination of claim 6, wherein the vessel contains milk and the predetermined temperature falls in a range of 160° to 162° F., inclusive.

8. The combination of claim 7, wherein the vessel further comprises:
a foldable bottom portion including the heat conductive laminate, wherein none of the vessel walls or the foldable bottom portion include a non heat-conductive portion;
heat sealed edges residing (i) in a single plane and (ii) along at least three sides of the vessel, the heat sealed edges being formed where the inner thermoplastic layers of the heat-conductive laminate are thermally bonded together.

9. A proof of treatment closure having an undeployed state and a deployed state, a distinction between the undeployed state and the deployed state being visible from outside a vessel, the proof of treatment closure including:
a cap configured to engage a vessel spout and form a hermetic seal therewith;
a barrel coupled to the cap and extending at least 20 mm therefrom;
a flag having a first position and a second position, the flag residing in the first position when the proof of treatment closure is in the undeployed state and in the second position when the proof of treatment closure is in the second state, wherein a status change from the undeployed state to the deployed state is achieved by heating a sensor disposed on the barrel to a predetermined temperature;
wherein the status change from the undeployed status to the deployed status is irreversible and the flag is inaccessibly sequestered within the closure.

10. The closure of claim 9, wherein the flag comprises a signal portion, the signal portion having low visibility when the closure is undeployed and being highly visible through a window in the cap when the closure is deployed.

11. The closure of claim 10, wherein:
the signal portion resides within the barrel when the closure is undeployed;
the window includes a transparent or translucent lens, and the signal portion is in direct contact with the lens when the closure is deployed;
the closure further comprises a transition medium and a spring, the transition medium residing in a bottom portion of the barrel and being adapted to undergo a physical transition at about the predetermined temperature;

the flag comprises an anchor portion, the anchor portion (i) being held fast in the transition medium when the flag is in the first position, and (ii) moving within the transition medium when the flag changes to the second position; and a force exerted on the flag by the spring moves the flag from the first position to the second position during the status change.

12. A method of using the closure of claim 10 comprising:
installing the closure of claim 10 on a vessel, the cap of the closure forming a hermetic seal with a vessel spout; and
heating the vessel until vessel contents reach a predetermined temperature and the flag adjusts from the first position to the second position.

13. A combination comprising:
a vessel comprising an internal cavity, vessel walls, a spout, and vessel contents residing in the internal cavity;
a proof of treatment closure having an undeployed state and a deployed state, a distinction between the undeployed state and the deployed state being visible from outside the vessel, the proof of treatment closure including:
  a cap threadably coupled directly to the spout and forming a hermetic seal therewith, the coupling between the cap and the spout being seal tamper evident;
  a barrel coupled to the cap and extending at least 20 mm into the vessel;
  a sensor (i) residing within the internal cavity and disposed on the barrel, and (ii) including a transition medium adapted to undergo a physical change at a predetermined temperature, wherein a change from the undeployed state to the deployed state is irreversibly achieved by heating the sensor to at least the predetermined temperature; and
  a flag inaccessibly sequestered within the proof of treatment closure, the flag:
    having a first position and a second position;
    residing in the first position when the proof of treatment closure is in the undeployed state and in the second position when the proof of treatment closure is in the deployed state,
    being resistant to status tampering; and
    including an anchor portion, the anchor portion being secured by the transition medium when the flag is in the first position and being at least partially removed from the transition medium when the flag is in the second position, wherein a change from the undeployed state to the deployed state is irreversibly achieved by heating the sensor to at least the predetermined temperature.

14. The combination of claim 13, wherein the vessel is flexible and collapsible, and the vessel walls comprise a heat conductive laminate including an inner thermoplastic polymer layer, a middle metal foil layer, and an outer polymer layer and heat sealed edges residing (i) in a single plane and (ii) along at least three sides of the vessel, the heat sealed edges being formed where the inner thermoplastic layers of the heat-conductive laminate are thermally bonded together.

* * * * *